United States Patent
Yang et al.

(10) Patent No.: US 7,920,928 B1
(45) Date of Patent: Apr. 5, 2011

(54) PASSIVE FIXATION FOR EPICARDIAL LEAD

(75) Inventors: Michael Yang, Thousand Oaks, CA (US); Wenbo Hou, Lancaster, CA (US); Sheldon Williams, Green Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 306 days.

(21) Appl. No.: 11/669,797

(22) Filed: Jan. 31, 2007

(51) Int. Cl.
*A61N 1/00* (2006.01)

(52) U.S. Cl. ....................................... 607/130

(58) Field of Classification Search .................. 607/115, 607/116, 119, 126, 129, 130, 132
See application file for complete search history.

(56) References Cited

U.S. PATENT DOCUMENTS

| | | | |
|---|---|---|---|
| 4,030,509 A | 6/1977 | Heilman et al. | |
| 4,142,530 A | 3/1979 | Wittkampf | |
| 4,235,246 A | 11/1980 | Weiss | |
| 4,299,239 A | 11/1981 | Weiss et al. | |
| 4,567,900 A * | 2/1986 | Moore | 607/129 |
| 4,620,550 A | 11/1986 | Doroshuk | |
| 4,860,769 A | 8/1989 | Fogarty | |
| 4,865,037 A | 9/1989 | Chin et al. | |
| 4,991,578 A | 2/1991 | Cohen | |
| 4,991,603 A | 2/1991 | Cohen et al. | |
| 4,998,975 A * | 3/1991 | Cohen et al. | 607/5 |
| 5,052,407 A * | 10/1991 | Hauser et al. | 607/125 |
| 5,143,090 A | 9/1992 | Dutcher et al. | |
| 5,217,028 A | 6/1993 | Dutcher et al. | |
| 5,336,252 A | 8/1994 | Cohen | |
| 5,387,233 A | 2/1995 | Alferness et al. | |
| 5,387,234 A * | 2/1995 | Hirschberg | 607/129 |
| 5,397,342 A * | 3/1995 | Heil et al. | 607/129 |
| 5,397,343 A | 3/1995 | Smits | |
| 5,425,756 A * | 6/1995 | Heil et al. | 607/128 |
| 5,653,734 A | 8/1997 | Alt | |
| 5,716,382 A | 2/1998 | Snell | |
| 5,871,532 A | 2/1999 | Schroeppel | |
| 5,897,586 A | 4/1999 | Molina | |
| 5,928,278 A * | 7/1999 | Kitschmann | 607/129 |
| 5,974,341 A | 10/1999 | Er et al. | |
| 6,539,944 B1 * | 4/2003 | Watson | 128/898 |
| 6,687,549 B1 | 2/2004 | Helland et al. | |
| 6,718,212 B2 | 4/2004 | Parry et al. | |

(Continued)

FOREIGN PATENT DOCUMENTS

WO 2004011081 A1 2/2004

(Continued)

OTHER PUBLICATIONS

D'Avila, Andre M.D. et al., "Pericardial Anatomy for the Interventional Electrophysiologist," J Cardiovasc Electrophysiol, vol. 14, pp. 422-430, Apr. 2003.

(Continued)

*Primary Examiner* — Mark W Bockelman
*Assistant Examiner* — Roland Dinga

(57) ABSTRACT

An epicardial lead is passively fixed in a pericardial space by a passive fixation member. The passive fixation member extends from a distal portion of an epicardial lead and acts against a pericardial layer and an epicardial layer to hold the lead in place. The epicardial lead may include an electrode that is connected to a conductor that extends from a distal portion of the lead. In some embodiments the epicardial lead includes a material that promotes fibrosis to fix the lead to heart tissue. The passive fixation member may include a shocking coil.

19 Claims, 14 Drawing Sheets

U.S. PATENT DOCUMENTS

| | | |
|---|---|---|
| 6,837,848 B2 | 1/2005 | Bonner et al. |
| 2003/0040787 A1 | 2/2003 | Flynn et al. |
| 2003/0074041 A1* | 4/2003 | Parry et al. .................... 607/130 |
| 2003/0114908 A1 | 6/2003 | Flach |
| 2004/0054391 A1 | 3/2004 | Wildon |
| 2004/0127967 A1 | 7/2004 | Osypka |
| 2004/0267338 A1* | 12/2004 | Harrison ....................... 607/105 |
| 2005/0102010 A1 | 5/2005 | Lau et al. |
| 2005/0102011 A1 | 5/2005 | Lau et al. |
| 2005/0102012 A1 | 5/2005 | Lau et al. |
| 2005/0102014 A1* | 5/2005 | Lau et al. ..................... 607/129 |
| 2005/0113900 A1* | 5/2005 | Shiroff et al. ................. 607/130 |
| 2005/0288715 A1 | 12/2005 | Lau et al. |
| 2006/0009831 A1 | 1/2006 | Lau et al. |

FOREIGN PATENT DOCUMENTS

| | | |
|---|---|---|
| WO | 2005046789 A1 | 5/2005 |
| WO | 2005092431 A1 | 10/2005 |

OTHER PUBLICATIONS

NonFinal Office Action, mailed May 5, 2009—Related U.S. Appl. No. 11/626,132.

Final Office Action, mailed Nov. 2, 2009—Related U.S. Appl. No. 11/626,132.

NonFinal Office Action, mailed Feb. 25, 2010— Related U.S. Appl. No. 11/626,132.

* cited by examiner

PASSIVE FIXATION FOR EPICARDIAL LEAD

TECHNICAL FIELD

This application relates generally to implantable cardiac devices and, in some embodiments, to an epicardial lead with passive fixation.

BACKGROUND

Implantable cardiac devices are used to treat a patient's heart that does not function normally due to, for example, a genetic or acquired condition. A typical implantable cardiac device may perform one or more functions including sensing signals generated in the heart, pacing the heart to maintain regular contractions and providing defibrillation shocks to the heart. Various techniques have been used to implant a cardiac device and associated cardiac leads.

An endocardial implantation technique generally involves gaining access to the interior of the heart via the venous return and implanting one or more leads within the heart. For example, an implantable device including circuitry for sensing signals from and generating stimulation signals for the heart may be subcutaneously implanted in the pectoral region of the patient. Leads connected to the device are routed from the device through a vein to the right side of the heart. A distal end of the lead may then be passively or actively attached to an inner wall of the heart.

An epicardial implantation technique generally involves implanting leads at an outer layer of the heart (e.g., on the epicardium). Advantageously, this technique may enable a physician to place a lead over any of the four chambers of the heart. Traditionally, an implantable device including the sensing and pacing circuitry is implanted in the abdominal region or the pectoral region of the patient. Here, sensing and stimulation leads are routed from the device to the epicardium via an appropriate path.

In addition, some form of fixation mechanism is provided for the epicardial-type lead. For example, a myo-epicardial lead may be fixed in place by screwing a helical electrode into myocardium. An epicardial lead may be fixed in place by suturing or gluing the electrodes onto the epicardial surface. Each of these techniques, however, generally involves an invasive procedure and direct visualization to ensure safety. For example, it is important to avoid damaging any of the arteries on the epicardial surface.

SUMMARY

A summary of various aspects and/or embodiments of an apparatus constructed or a method practiced according to the invention follows. For convenience, one or more embodiments of an apparatus constructed or a method practiced according to the invention may be referred to herein simply as an "embodiment."

The invention relates in some aspects to passively fixing an implantable epicardial lead in the pericardial space. In some embodiments a passive fixation mechanism acutely fixes the lead in place thereby enabling natural body processes to chronically fix the epicardial lead to heart tissue over time. In some embodiments provisions are made to promote such chronic fixation.

In some embodiments a passive fixation member extends from a distal portion of an implantable epicardial lead and mechanically acts against an outer pericardial layer and an epicardial layer to hold the epicardial lead in place. For example, the fixation member may be predisposed to orient to a shape that serves to securely hold the fixation member between the pericardial and epicardial layers. Moreover, the fixation member may be adapted to spring back in response to mechanical deformation that results from force exerted on the fixation member by the pericardial and epicardial layers. In this way, the fixation member may effectively be wedged between the layers by, for example, frictional force.

In some embodiments the implantable epicardial lead includes a cardiac pacing and/or sensing electrode. The electrode may be connected in some cases to a conductor that extends from the distal portion of the implantable epicardial lead. In addition, one or more structural support members may be used to fix the electrode relative to the fixation member.

In some embodiments the implantable epicardial lead includes a material (e.g., a thrombotic material) that promotes fibrosis to fix the implantable cardiac lead to heart tissue. This material may be incorporated into one or more components of the implantable epicardial lead. For example, the material may be in the form of a mesh or suture that is wrapped around or extends from a component of the implantable epicardial lead. In some embodiments the material comprises a polyester material, a polymer material or a suture material.

In some embodiments the fixation member comprises a coil for providing shocks (e.g., anti-tachycardia shocks) to the heart. The shocking coil may be shaped such that a coil having a relatively small cross section provides an effective shocking potential to the heart.

In some embodiments the fixation member may be predisposed to define a closed or semi-closed shape. For example, the fixation member may define a complete loop shape or a partial loop shape.

In some embodiments an implantable epicardial lead including one or more of the components described above may be adapted for implant into the pericardial space via a relatively non-invasive technique. For example, a proximal portion of the lead may be inserted into the pericardial space via a delivery instrument that is inserted into a patient using a subxiphoid or similar technique. Accordingly, the fixation member and other components may be adapted to reorient in shape to facilitate inserting the epicardial lead into the delivery instrument.

BRIEF DESCRIPTION OF THE DRAWINGS

These and other features, aspects and advantages of the invention will be more fully understood when considered with respect to the following detailed description, appended claims and accompanying drawings, wherein:

FIG. 9, including

FIG. 10, including

FIG. 15, including

Figure 2:
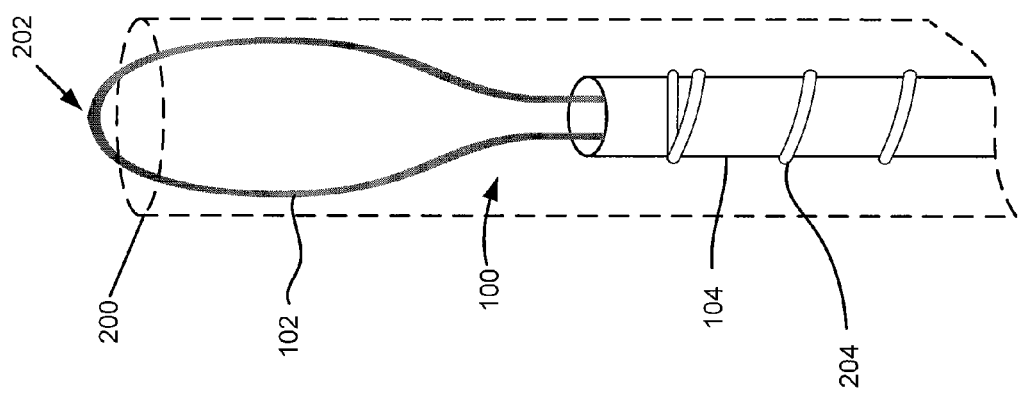
FIG. 2 is a simplified diagram of an embodiment of an implantable epicardial lead inserted into a delivery instrument.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The invention is described below, with reference to detailed illustrative embodiments. It will be apparent that the invention may be embodied in a wide variety of forms, some of which may appear to be quite different from those of the disclosed embodiments. Consequently, the specific structural and/or functional details disclosed herein are merely representative and do not limit the scope of the invention. For example, based on the teachings herein one skilled in the art should appreciate that the various structural and/or functional details disclosed herein may be incorporated in an embodiment independently of any other structural and/or functional details. Thus, an apparatus may be implemented and/or a method practiced using any number of the structural and/or functional details set forth in any disclosed embodiment(s). Also, an apparatus may be implemented and/or a method practiced using other structural and/or functional details in addition to or other than the structural and/or functional details set forth in any disclosed embodiment(s).

Figure 1:
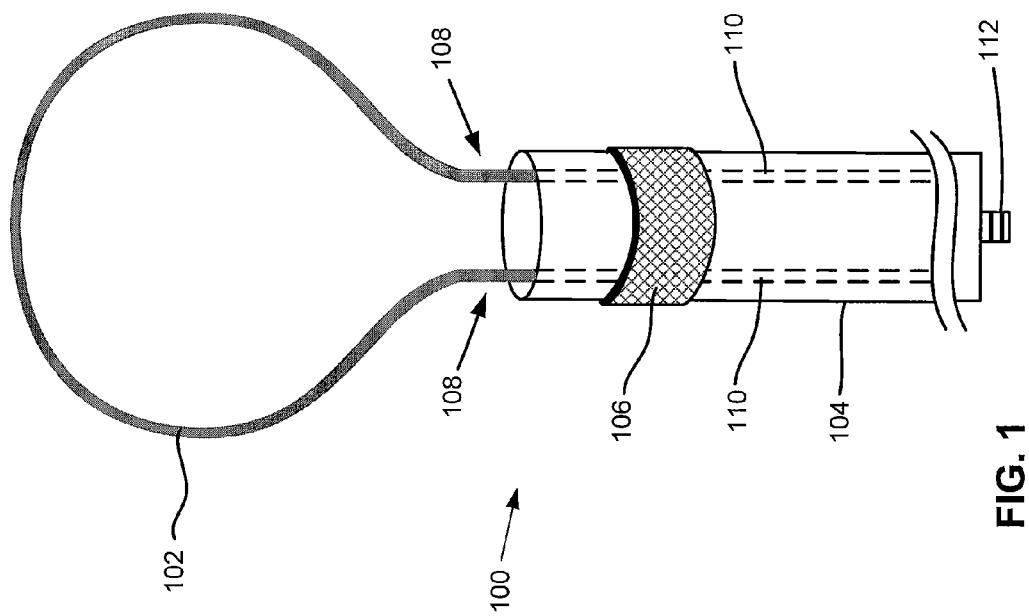
FIG. 1 is a simplified diagram of an embodiment of an implantable epicardial lead including a passive fixation member.

FIG. 1 illustrates an embodiment of an epicardial lead 100 including a passive fixation member 102. In this example, the fixation member 102 extends from a distal portion (e.g., the distal end) of a lead body 104 of the epicardial lead 100 and expands outwardly to define a closed shape. As will be discussed in more detail below, the fixation member 102 may comprise a relatively thin and elongated structure. Accordingly, the fixation member 102 may provide a relatively flat profile along the dimension parallel with the page of FIG. 1.

Moreover, the fixation member 102 may be constructed in a manner that provides a desired degree of flexibility and resiliency. For example, in some embodiments the fixation member 102 may be adapted to spring back in response to mechanical deformation caused by a force applied in a direction substantially perpendicular to the closed shape (e.g., toward the page in FIG. 1). Accordingly, when the fixation member 102 is inserted into a curved pericardial space (not shown in FIG. 1), the interaction of the outer pericardial layer and the epicardial layer with the fixation member 102 will tend to bend the fixation member 102. Due to the resiliency of the fixation member 102, the fixation member 102 will impart a complementary force on the pericardial and epicardial layers. This in turn may increase the friction between the fixation member 102 in the pericardial and epicardial layers such that the friction will impede movement of the fixation member 102 in a lateral direction within the pericardial space. Consequently, the fixation member 102 may provide an effective mechanism to passively hold the epicardial lead 100 in position in the pericardial space.

FIG. 1 also illustrates that the epicardial lead 100 may include one or more components that acutely provide additional friction with surrounding tissue and chronically promote fibrosis (e.g., fibrous growth on the lead 100 and/or its components) to provide additional mechanical support for the epicardial lead 100 in the pericardial space. For example, a thrombotic material 106 having in some embodiments a relatively rough and porous outer surface may be attached to an outer surface of the lead body 104. The material 106 may comprise, for example, a mesh material such as polyester (e.g., Dacron), a polymer, a suture material or some other suitable material. When the epicardial lead 100 is implanted in the pericardial space, the rough outer surface of the material 106 will provide additional friction between the epicardial lead 100 and the surrounding outer pericardial layer and the epicardial layer. In addition, the body will react to the presence of the foreign thrombotic material 106 by forming a tissue layer over the foreign material. Accordingly, the material 106 may serve to speed up the process by which the epicardial lead 100 may be fixed to heart tissue (e.g. the epicardial layer) by the fibrosis process.

From the above it may be appreciated that the combination of the passive fixation member 102 and the thrombotic material 106 may provide an effective mechanism to passively fix the epicardial lead 100 in the pericardial space. Here, the fixation member 102 may provide acute and/or chronic fixation to hold the epicardial lead 100 in place. In addition, the material 100 may provide acute fixation and initially promote the fibrosis process to provide additional support to acutely fix the epicardial lead 100 in place.

In some embodiments the fixation member 102 may comprise a coil electrode that may be used to apply shocking therapy to the heart. For example, a coil electrode may be used in conjunction with other coil electrodes (e.g., as discussed herein) and/or with other electrodes such as the "case" of an implantable cardiac device. Advantageously, a shocking coil configured to take the form of a closed or semi-close shape as taught herein may provide a defibrillation threshold ("DFT") comparable to a DFT provided by a larger conventional patch shock electrode. For example, in some embodiments it may be possible to obtain sub-10 joule DFTs (e.g., on the order of 3 joules) and/or shocking efficiency of up to approximately 98%.

In some embodiments the fixation member 102 may comprise or include one or more electrical conductors (e.g., a multi-strand coil conductor). In this case, one or both ends 108 of the fixation member 102 may comprise or couple with an electrical conductor 110 that is routed through the lead body 104. After implant, the electrical conductor 110 is coupled to, for example, an implantable cardiac device (not shown) via one or more connectors (e.g., connector 112) at the proximal end of the epicardial lead 100.

The fixation member 102 also may be sufficiently flexible in the appropriate dimensions so that its cross-section may be temporarily reduced to facilitate routing the epicardial lead 102 to an implant site via a relatively thin delivery instrument 200 as shown in FIG. 2. For example, in some embodiments the epicardial lead 102 may be routed through an introducer or other suitable instrument having a diameter on the order of 14 French or less. To more clearly show the epicardial lead 100 in FIG. 2, the delivery instrument 200 is shown in dashed form rather than the epicardial lead 100. It should be understood, however, that the lead body 104 and the fixation member 102 are adapted to slide within a lumen defined by the delivery instrument 200.

In some embodiments the fixation member 102 is adapted to be sufficiently flexible and resilient such that the shape of the fixation member 102 may be oriented between a predisposed expanded shape (e.g., as shown in FIG. 1) and an elongated shape (e.g., as shown in FIG. 2). For convenience, the size of the lead 100 has been reduced in FIG. 2. FIG. 2 also illustrates that the fixation member 102 may include one or more discontinuities such as, for example, a predisposed bend 202 that facilitates bending the fixation member 102 in a given manner.

Finally, FIG. 2 shows another example of a thrombotic material that may be incorporated into the epicardial lead 100. In this case, a suture wrap 204 has been wrapped around a distal portion of the lead body 104. Accordingly, the suture wrap 204 may promote fibrosis upon implant. The suture wrap 204 may be constructed of any conventional suture material or some other suitable thrombotic material (e.g., as discussed herein).

Figure 3:
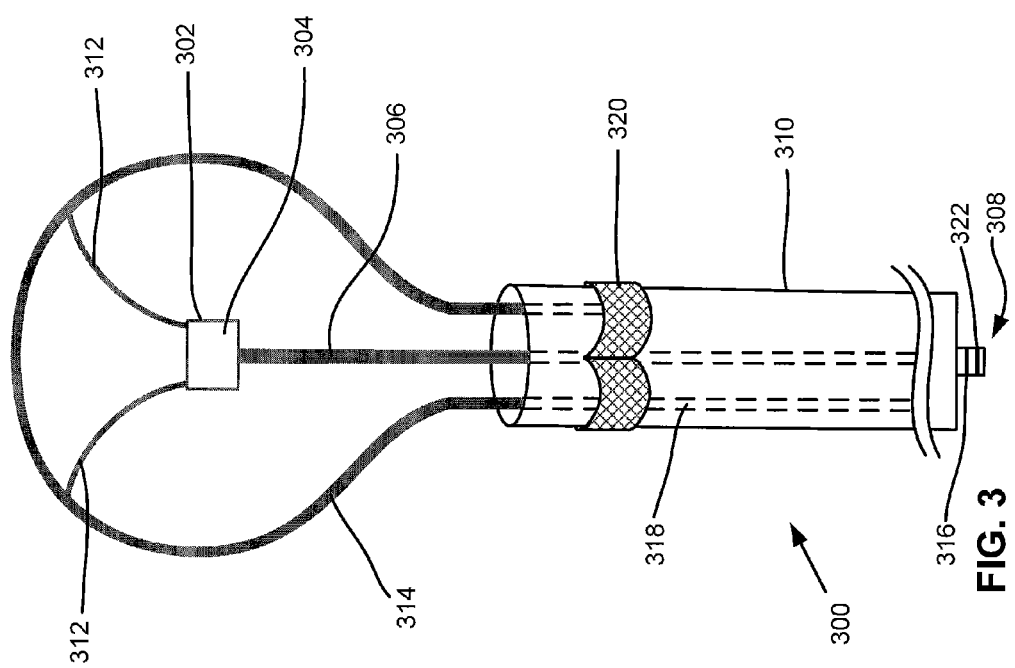
FIG. 3 is a simplified diagram of an embodiment of an implantable epicardial lead including an electrode.

Referring now to FIG. 3, in some embodiments an epicardial lead 300 may incorporate one or more electrodes (which may be referred to hereafter, for convenience, as "the electrode") 302. The electrode 302 may be used, for example, to sense conditions in a patient's heart (not shown) and/or to provide pacing signals to the patient's heart. Accordingly, the electrode 302 may be oriented on the epicardial lead 300 such that a surface 304 of the electrode makes contact with the epicardial surface (not shown in FIG. 3) when the epicardial lead 300 is implanted in the pericardial space.

The electrode 302 may take various forms. For example, in some embodiments the electrode 302 may have an elliptical shape. In other embodiments the electrode may have a mushroom-like shape, where the "head" of the mushroom shape faces downward and contacts the epicardial surface during pacing or sensing events. In some embodiments the orientation of the electrode may be bidirectional or unidirectional.

The electrode 302 may be configured as a unipolar electrode, a bipolar electrode or in some other manner. For example, the electrode 302 may be used in conjunction with another electrode on the epicardial lead 100 (e.g., as discussed herein), with another electrode on another lead, with the "case" of an implantable cardiac device, with a conductive passive fixation member 314 (e.g., a shocking coil) or with any other suitable electrode.

One or more conductors (which may be referred to hereafter, for convenience, as "the conductor") 306 may couple the electrode 302 to one or more connectors (e.g., connector 308) at a proximal end of the epicardial lead 300. In the example of FIG. 3, the conductor 306 is routed through a lead body 310 of the epicardial lead 300 and extends from a conductor 322 on the connector 308 to the electrode 302.

In some embodiments one or more structural support members 312 maintain the electrode 302 in place relative to the passive fixation member 314 and/or some other component(s) of the epicardial lead 300. For example, the structural support member 312 may hold the electrode 302 at an interior of a closed shape defined by the fixation member 314. In addition, the structural support member 312 may maintain the electrode 302 at a desired orientation to facilitate mating the surface 304 with epicardial tissue. To this end, in the example of FIG. 3 one end of the structural support member 312 is coupled to the electrode 302 and another end of the structural support member 312 is coupled to the fixation member 314. A structural support member 312 also may serve to support the elongated fixation member 314 and/or facilitate expanding the elongated fixation member 314 back to its predisposed shape after a delivery tool (e.g., a stylet) has been withdrawn from the lead 300.

To accommodate the distortion of the fixation member 314 when the epicardial lead 300 is routed through a delivery instrument (not shown) at least a portion of the support member 312 may be flexible and resilient. For example, in some embodiments the entire support member 312 may be relatively flexible. Alternatively, a substantially rigid support member 312 may have flexible ends and/or may be flexibly attached to the electrode 302 and/or the fixation member 314.

A passive fixation member 314 may be constructed of various materials. For example, the passive fixation member 314 may be constructed of one or more polymers, one or more metals, or some combination of these materials. In some embodiments the passive fixation member 314 may be constructed of a conventional lead material such as silicone, polyurethane, etc. In some embodiments, at least a portion of the fixation member 314 may comprise a bare conductive coil (e.g., constructed using materials such as platinum, MP35N, Nitinol, conductive silicone, etc.) to provide shocking therapy. It should thus be appreciated that a passive fixation member as taught herein may be constructed in a variety of ways and using various materials beyond those specifically described herein.

FIG. 3 illustrates that in some embodiments an electrically conductive fixation member 314 may be coupled to a conductor 316 on the connector 308 at a proximal end of the epicardial lead 300 via a single conductor 318. In this case, one of the ends of the fixation member 314 may simply be mechanically fixed to the lead body 310. For example, in some embodiments a clamp 320 or other suitable mechanism may be used to mechanically fix (e.g., provide strain relief for) the fixation member 314 and/or the conductor 306 to the lead body 310. In addition, in some embodiments the two ends of the fixation member 314 may be electrically connected together.

Figure 4:
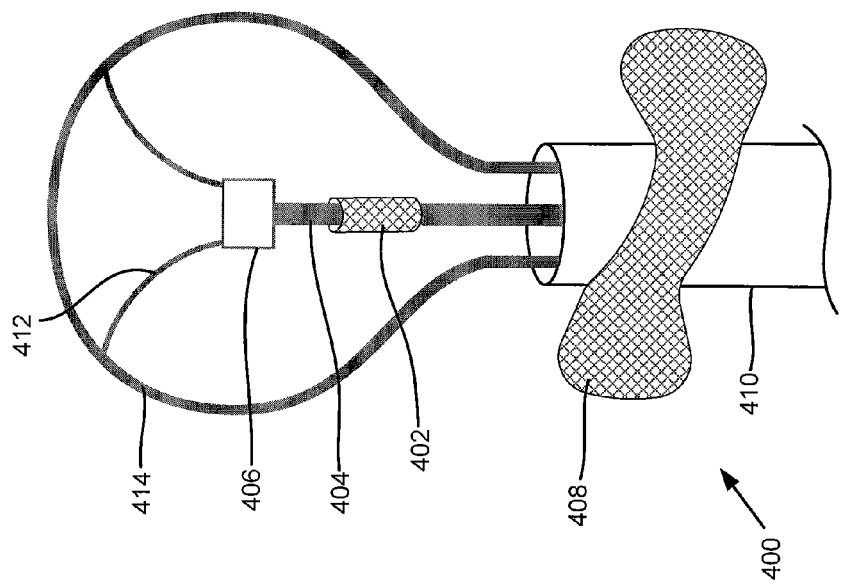
FIG. 4 is a simplified diagram of an embodiment of an implantable epicardial lead including a material for promoting fibrosis.

Referring now to FIG. 4, it should be appreciated based on the teachings herein that a variety of mechanisms may be incorporated into an epicardial lead to facilitate chronic fixation of the epicardial lead within the pericardial space. FIG. 4 illustrates two additional examples of components and materials that may be incorporated into an epicardial lead 400.

In some embodiments a thrombotic material 402 (e.g., a mesh material) may be incorporated into (e.g., wrapped around) at least a portion of a conductor 404 for an electrode 406. Here, when the distal portion of the epicardial lead 400 is inserted into the pericardial space, the thrombotic material 402 is positioned against the epicardial surface to promote tissue growth on and/or through the material 402.

In some embodiments a thrombotic material 408 (e.g., a mesh material) formed in a flap-like or wing-like structure may extend from a distal portion of a lead body 410 of the epicardial lead 400. Here, the material 408 may be folded and/or wrapped around the lead body 410 when the distal portion of the lead 400 is routed through the delivery instrument (not shown). Once the distal end of the delivery instrument is withdrawn from the pericardial space, the material 408 may be unfolded and/or unwrapped from the lead body 410. The material 408 may thus be laid out over the epicardial surface to promote tissue growth on and/or through the material 408.

A fibrosis-promoting material as described herein may be incorporated into any component of an epicardial lead. For example, in some embodiments such a material may be incorporated into one or more of a lead body, a conductor, a passive fixation member, a structural support member, or any other suitable component of an epicardial lead.

Figure 6:
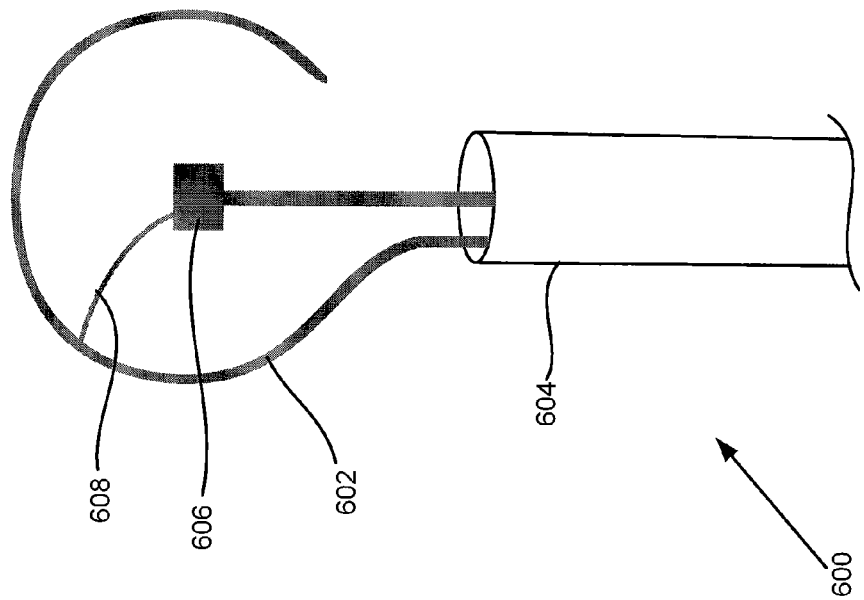
FIG. 6 is a simplified diagram of an embodiment of an implantable epicardial lead including a passive fixation member defining a semi-closed shape.
Figure 5:
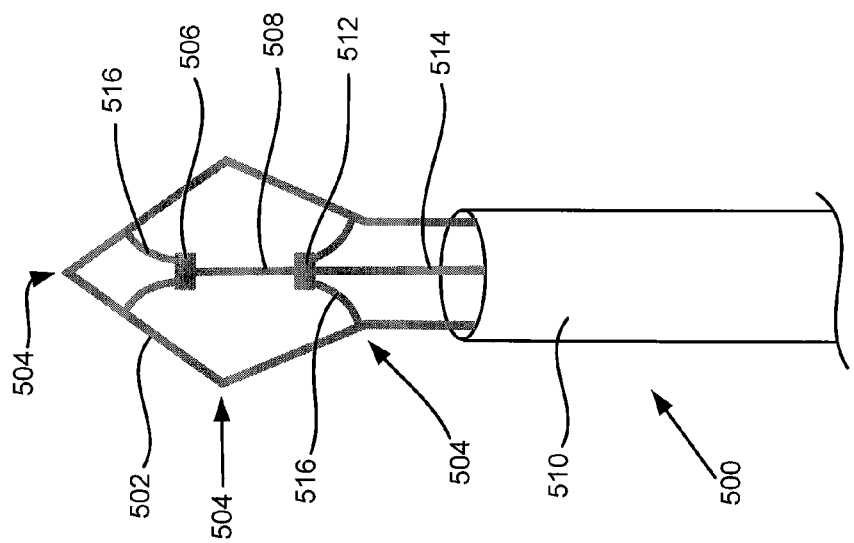
FIG. 5 is a simplified diagram of an embodiment of an implantable epicardial lead including a passive fixation member having sharp bends.

Referring now to FIGS. 5 and 6, a passive fixation member may be adapted to define a wide variety of closed or open (e.g., semi-closed), two-dimensional or three-dimensional shapes. Accordingly, desired mechanical and/or electrical characteristics for the fixation member may be obtained by appropriate choice of the size, shape, structure, etc., of the fixation member (e.g. a mechanical fixture or a shocking coil). It should be appreciated that the examples shown herein are but a few examples of closed or open shapes that may be defined by a passive fixation member incorporated into an epicardial lead and that many other shapes may be used in accordance with the teachings herein.

FIG. 5 illustrates an embodiment where an epicardial lead 500 includes a passive fixation member 502 that incorporates a plurality of predisposed bends 504, thereby defining a relatively complex closed shape. Here, the predisposed bends 504 may facilitate reorientation of the fixation member 502 between an expanded shape as shown in FIG. 5 and a collapsed (e.g., elongated) shape for insertion into a delivery instrument (not shown).

FIG. 5 also illustrates an embodiment of an epicardial lead 500 that incorporates more than one electrode. For example, a first electrode 506 may be coupled to a first conductor 508 that is routed through a lead body 510 of the epicardial lead 500. A second electrode 512 may be coupled to a second conductor 514 that also is routed through the lead body 510. Such a configuration may be used, for example, to improve or modify the unipolar cardiac sensing or pacing capability of the epicardial lead 500 and/or to provide bipolar cardiac sensing or pacing. It should be appreciated that a different number of electrodes (e.g., two, four or more) may be incorporated into an epicardial lead depending upon the requirements of a given application.

FIG. 6 illustrates an embodiment of an epicardial lead 600 including a passive fixation member 602 that defines an open (e.g., semi-closed) shape. In this case, the fixation member 602 may be attached to a lead body 604 of the epicardial lead at a single location. FIG. 6 also illustrates that an epicardial lead defining an open shape may include one or more electrodes 606. For example, one or more structural support members 608 may hold the electrode 606 in place relative to the fixation member 602 or other components of the epicardial lead 600.

FIGS. 5 and 6 further illustrate that a structural support member may take a variety of forms. For example, the epicardial lead 500 of FIG. 5 incorporates four structural support members 516. In contrast, the epicardial lead 600 of FIG. 6 incorporates a single structural support member 608. In addition, it should be understood that a structural support member may be coupled to components other than those specifically shown herein. For example, in some embodiments a structural support member may be coupled to a conductor and/or to a lead body.

Through the use of an open shape as shown, for example, in FIG. 6, a passive fixation member may be advantageously adapted to more readily reorient between an expanded shape and an elongated shape. For example, referring to FIGS. 7 and 8 it may be seen that an open shape may be readily bent to a substantially linear shape.

Figure 8:
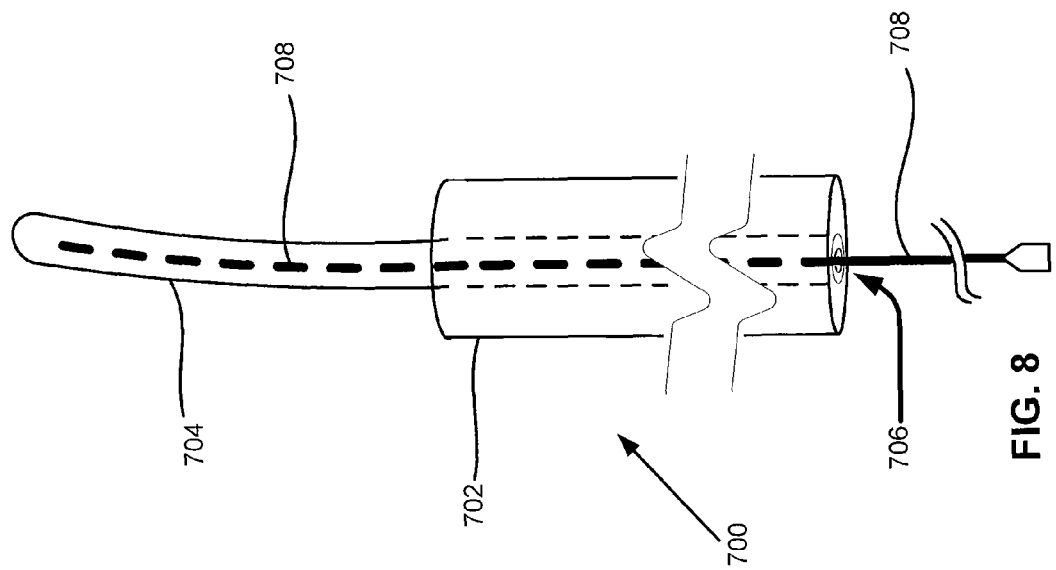
FIG. 8 is a simplified diagram of an embodiment of an implantable epicardial lead illustrating how a stylet may be used to straighten a passive fixation member.
Figure 7:
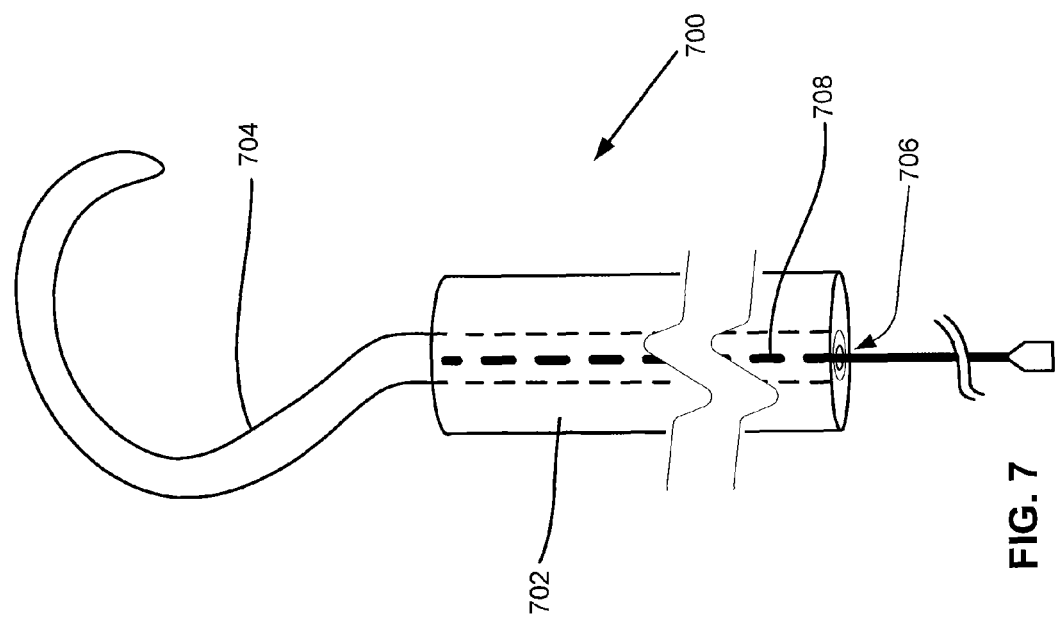
FIG. 7 is a simplified diagram of an embodiment of an implantable epicardial lead including a passive fixation member defining a lumen for a stylet.

In some embodiments an epicardial lead and associated passive fixation member may be adapted to accept a stylet that may be used to straighten the fixation member. For example, as shown in FIG. 7 a lead body 702 and a passive fixation member 704 of an epicardial lead 700 may define a lumen 706 adapted to receive a stylet 708 or other suitable elongated member. As shown in FIG. 8, when the stylet 708 is inserted through the lead body 702 and into the passive fixation member 704 the stiffness of the stylet 708 causes the normally curved fixation member 704 to straighten (e.g., to a less curved shape such as a substantially linear shape). Consequently, such a configuration may enable the use of a relatively large shape that may nonetheless be inserted into a delivery instrument with relative ease since the shape may be readily straightened.

It should be appreciated that when the defined shape is substantially (e.g., almost) closed, the electrical characteristics (e.g., shocking coil characteristics) of the fixation member may be substantially identical to the electrical characteristics of a similar closed shape (e.g., a loop). Accordingly, a fixation member defining an open shape may advantageously provide the desired support and/or electrical characteristics while providing the above or other advantages.

A stylet also may be advantageously used in conjunction with other predisposed shapes of the fixation member. For example, referring to the cross-section view of a lead body 900 shown in FIG. 9A, one or more lumens (e.g., lumens 902 and 904) may be provided in the lead body 900 and adapted to carry section 912 and 914 of a fixation member. The sections 912 and 914 also may include lumens 916 and 918, respectively, to enable a stylet (not shown) to be routed through one or more sides of the fixation member (e.g., defining a closed shape).

Figure 9A:
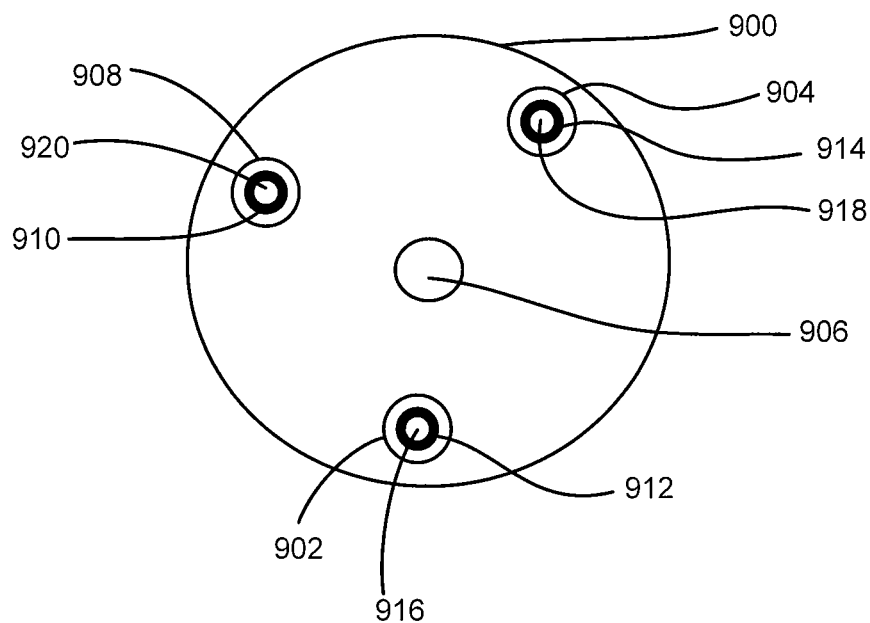
FIGS. 9A and 9B, depicts a simplified diagram of a cross section of an embodiment of an implantable epicardial lead incorporating conductors with lumens and a simplified diagram of an embodiment of an implantable epicardial lead incorporating coiled conductors.
Figure 9B:
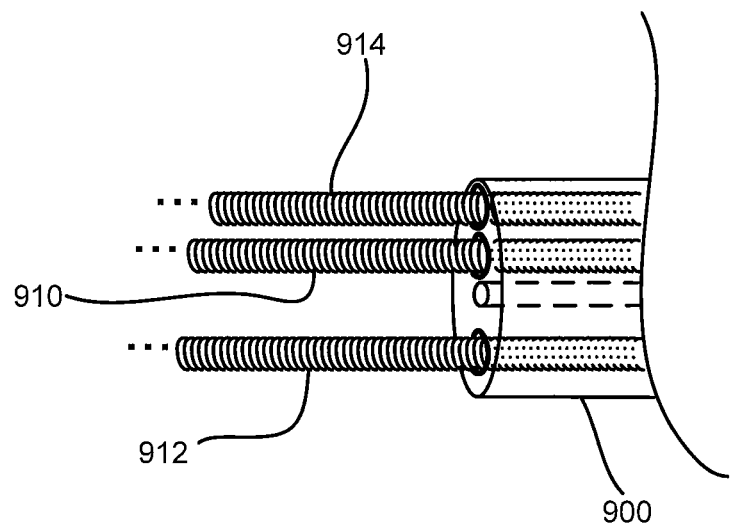

FIG. 9B illustrates an embodiment where a fixation member comprises a coil conductor that defines a closed loop shape. For convenience, only two end sections 912 and 914 of the loop shape are shown in FIG. 9B. As shown in FIG. 9A, the respective end sections 912 and 914 may be routed through the lead body 900 to the proximal end of the lead body 900. A stylet may thus be inserted into one or both of the lumens 916 and 918 defined in the sections 912 and 914 of the coil conductor. The distal end of the stylet may thus be routed through the sections 912 and 914, close to a midpoint (e.g., bend 202 in FIG. 2) of the closed shape to orient the fixation member to an elongated (e.g., more linear) shape.

FIG. 9 also illustrates that the lead body 900 may define other lumens. For example, the lead body 900 may define a lumen 906 for a stylet or similar apparatus (not shown) that may be used to steer or otherwise manipulate the lead body 900 during the implant procedure. In addition, the lead body 900 may define a lumen 908 for a conductor 910 that extends from the distal portion of the lead body 900. The conductor 910 also may include a lumen 920 adapted to receive a stylet or similar apparatus that may be used to manipulate the conductor 910.

Figure 10A:
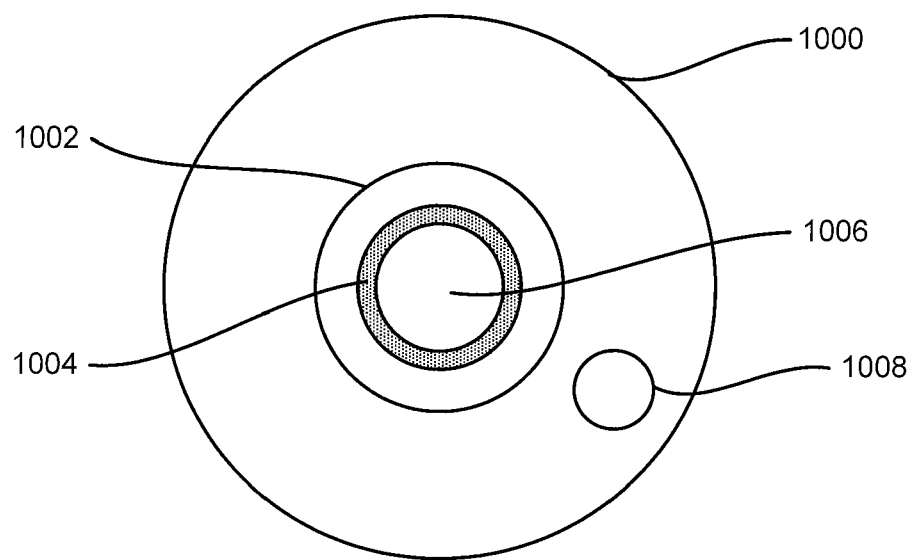
FIGS. 10A and 10B, depicts a simplified diagram of a cross section of an embodiment of an implantable epicardial lead and a simplified diagram of an embodiment of an implantable epicardial lead incorporating a looped passive fixation member.

FIG. 10 illustrates an embodiment of a lead 1000 that includes a central lumen 1002 adapted to receive a coiled passive fixation member 1004. The member 1004 includes a lumen 1006 adapted to receive a stylet. The lead 1000 also may include one or more lumens (e.g., lumen 1008) adapted to carry one or more conductors that attach to one or more pacing and/or sensing electrodes (not shown).

Figure 10B:
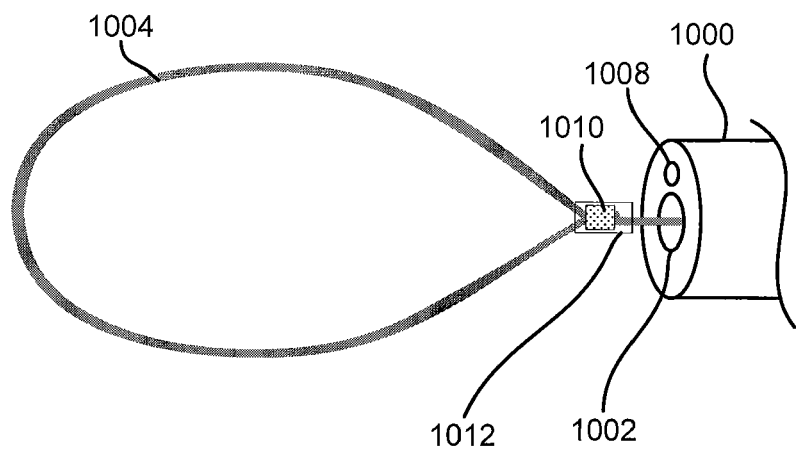

FIG. 10B illustrates that the distal end of the member 1004 may looped back and attached to another portion of the member 1004 via a mechanism 1010 such as a crimp, a clamp, or via some other suitable technique. In addition, a boot 1012 (e.g., constructed of a lead material such as silicone, etc.) may be provided over the mechanism 1010 for protection and/or additional mechanism support. In this embodiment a stylet (not shown) may be used to facilitate inserting the member 1004 into the lumen 1002. Here, the stylet may be inserted into a proximal end of the lumen 1006 and routed to the distal portion of the member 1004, thereby causing the loop to flatten out.

Figure 11:
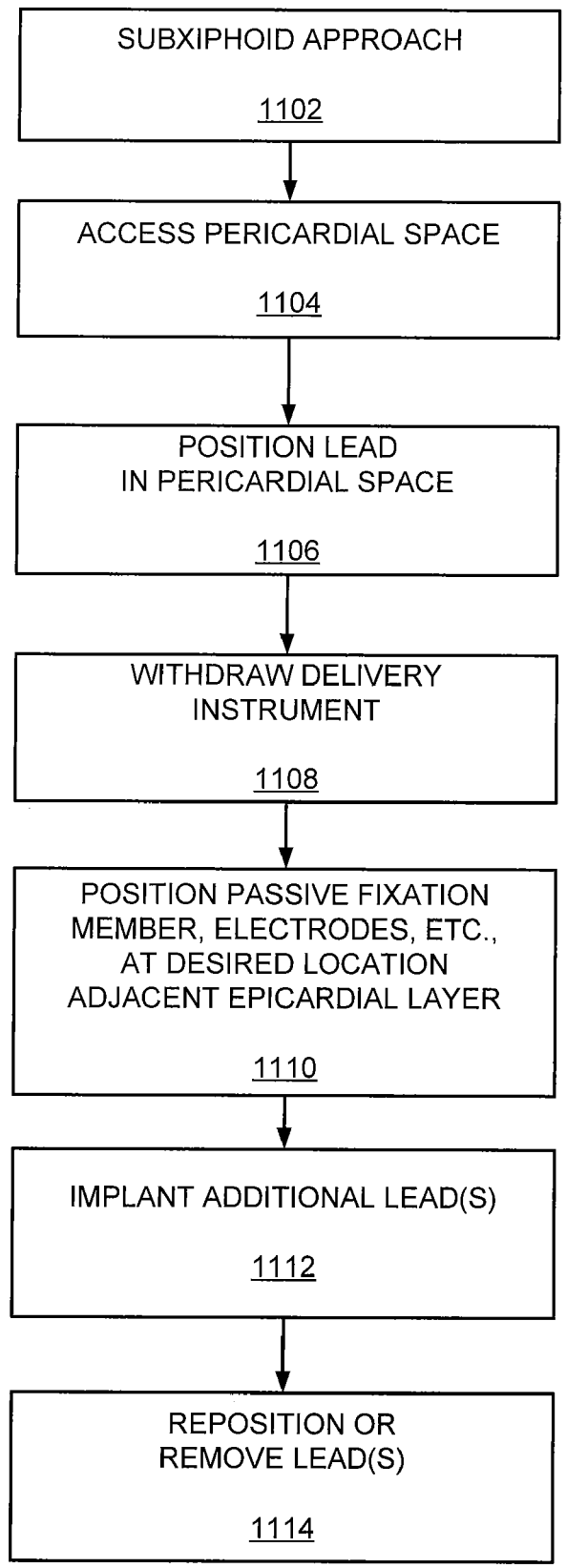
FIG. 11 is a flow chart of an embodiment of operations that may be performed to implant one or more epicardial leads.

With the above overview in mind, an embodiment of operations that may be performed to implant an epicardial lead will be discussed in conjunction with FIG. 11. For convenience, the operations of FIG. 11 may be described in conjunction with specific embodiments described herein. It should be appreciated, however, that these operations may be performed in conjunction with or using other components.

Figure 12:
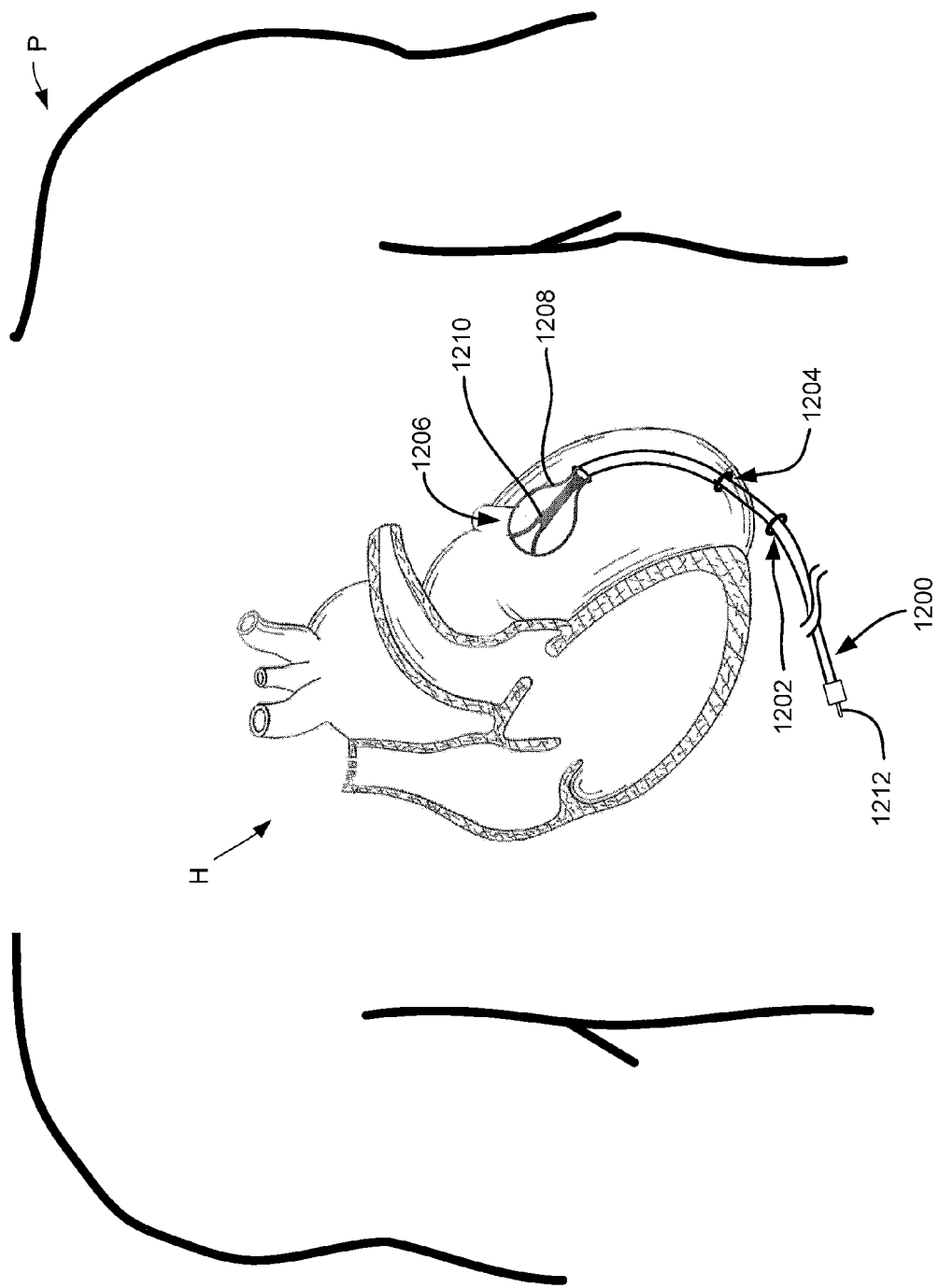
FIG. 12 is a simplified diagram of an embodiment of an epicardial lead implanted via a subxiphoid approach.

As represented by block 1102, a physician or electrophysiologist (referred to hereafter for convenience as "the physician") may use a relatively minimally-invasive subcutaneous procedure such as a subxiphoid approach or an intercostal approach to route a lead to the pericardium of a heart H of a patient P as shown in FIG. 12. FIG. 12 illustrates in a simplified manner a lead implanted in the pericardial space. For convenience, the lead 1200 is not shown in dashed form. It should be appreciated that the illustrated subcutaneous implantation technique is but one example of a technique that may be used in conjunction with implantation of an epicardial lead. Thus, techniques other than those specifically described herein may be used to access the pericardium.

Referring to FIG. 12, a conventional subxiphoid approach may involve routing a needle (not shown) through an incision 1202 in a mid-chest area of a patient P, into the thoracic cavity and to the pericardium. In practice, one or more incisions 1202 may be made in an area below the sternum during the procedure. The location and size of each incision and the types of instruments used during the procedure may vary depending upon the patient's anatomy and the preferences of the physician. Each incision may accommodate a trocar (not shown) for facilitating the insertion and manipulation of one of the instruments.

The attending physician uses the needle to puncture a hole 1204 in the pericardium then advances a guidewire (not shown) through the needle and into the pericardial space. After removing the needle, the physician routes an introducer/dilator (not shown) over the guidewire to advance the introducer through a resulting enlarged hole in the pericardium.

As represented by block 1104, the dilator is removed to enable a physician to route an epicardial lead 1200 through the introducer (e.g., delivery instrument). When the epicardial lead 1200 (which is straightened by a stylet) is inserted into the delivery instrument, the associated passive fixation member is bent to an elongated shape (not shown) to reduce the cross-sectional area of the passive fixation member.

The distal portion of the lead 1200 is routed via the delivery instrument through the body of the patient and into the pericardial space. Various imaging techniques may be used during the implant procedure. In some embodiments, an instrument (e.g., as discussed above) used during implant and/or the lead 1200 may include markers that enable the physician to observe the location of the instrument/lead using, for example, fluoroscopy. Alternatively, imaging techniques such as echography, MRI, endoscopy, X-ray, ultrasound, etc., may be used to track the location of an instrument/lead within the patient's epicardial space.

As represented by block 1106, the lead 1200 is then manipulated (e.g., using a stylet) to position the distal portion 1206 of the lead 1200 at a desired location in the pericardial space. Here, placing the distal portion 1206 at a desired position may entail positioning an electrode at an appropriate location adjacent a chamber or some other area of the heart where it is desirable to sense signals and/or generate stimulation signals.

In some embodiments imaging techniques may be used to verify that the lead 1200 is properly positioned and/or oriented in the pericardial space. For example, the position of the lead 1200 may be monitored using a fluoroscopy technique, an ultrasound technique, echography or some other suitable technique. In some embodiments, the lead 1200 and/or its thrombotic material components may incorporate imaging materials or components such as imaging markers to facilitate identifying the location and orientation of the lead 1200.

As represented by block 1108, the delivery instrument is removed leaving the lead 1200 in place. At this point, the passive fixation member 1208 on the lead 1200 will expand from the elongated shape to its pre-disposed expanded shape. For example, as shown in FIG. 12 the predisposed shape of the fixation member 1208 may be manipulated such that it lies flat against the epicardial layer in the pericardial space.

As represented by block 1110, the passive fixation member and/or any other component of the lead 1200 may be moved (e.g., using a stylet) to place the component at a desired location in the pericardial space. Here, the electrode 1210 and/or a shocking coil (e.g., member 1208) incorporated into the lead may be placed at a desired location adjacent to the epicardial layer to sense/stimulate the heart. These electrical components may then be coupled to an implantable cardiac device (not shown) by plugging a connector 1212 at the proximal end of the lead 1200 into the implantable cardiac device.

In addition, any material incorporated into the epicardial lead 1200 that promotes the fibrosis process may be appropriately positioned at this time. The passive fixation member 1208 may thus serve as an acute mechanism that temporarily holds the epicardial lead 1200 in place to provide sufficient time for tissue to form over the thrombotic material, the epicardial lead 1200 or any other component to provide the primary mechanism for chronically fixing the epicardial lead 1200 in the pericardial space.

As represented by block 1112, in some embodiments one or more additional epicardial leads may be implanted in the pericardial space. Advantageously, this may be accomplished via the same delivery instrument that was used to deliver the epicardial lead 1200. For example, in some embodiments the epicardial leads may each have an outer diameter on the order of 6 French while the delivery instrument has an internal dimension on the order of 14 French.

When multiple epicardial leads are used, shocking electrode pairs on the various leads may be placed in certain positions relative to one another (e.g., diametrically opposed across the heart). For example, in some embodiments a pair of shocking coils may be positioned opposite one another across the heart to enable the shocking pulse to travel through a significant portion of the right ventricle and the left ventricle. In some embodiments it may be desirable to use a larger shocking coil on the left side of the heart. For example, a first shocking coil of a given size may be positioned near an upper portion of the right ventricle (e.g., near the right atrium) while a second shocking coil having a larger size may be positioned near the lower apex of the left ventricle.

As represented by block 1114, in some cases it may be desirable or necessary to move or remove (e.g., explant) an implanted epicardial lead. For example, it may be desirable to move the implanted epicardial lead to a different location on the surface of the heart to improve sensing/stimulation performance. In some embodiments, an optimum position for an implanted epicardial lead may be identified by testing DFT at various locations of the epicardial lead along the epicardial surface.

Advantageously, due to the flexible characteristic of the passive fixation member, the fixation member may be reoriented to the elongated shape to facilitate removing the epicardial lead from the pericardium. For example, a stylet may be inserted into a lumen in the epicardial lead as discussed herein to facilitate straightening the bent shape of the fixation member.

Figure 13:
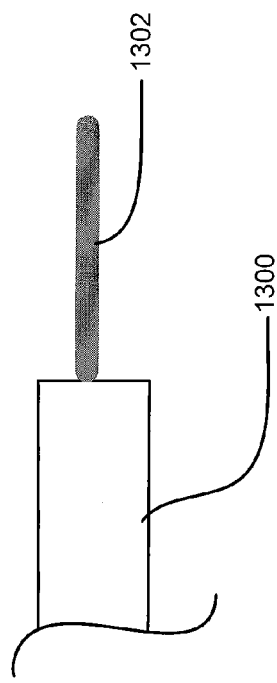
FIG. 13 is a simplified diagram of a view illustrating a flat profile of an embodiment of an implantable epicardial lead.
Figure 14:
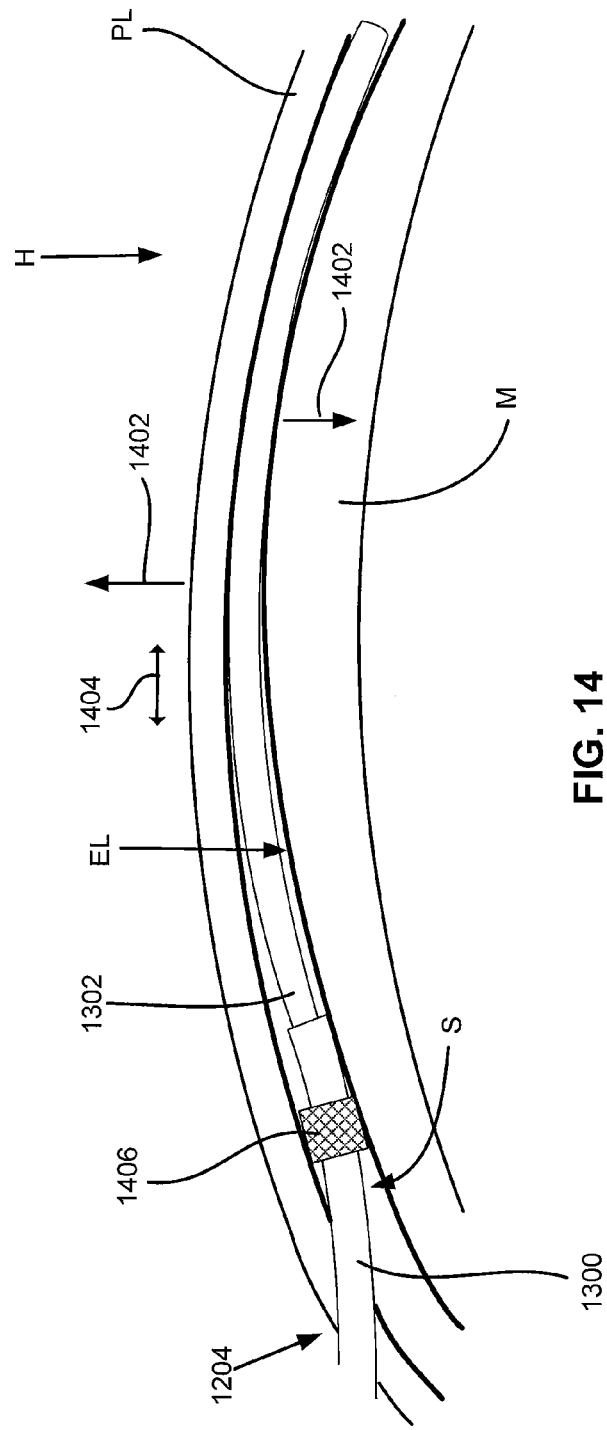
FIG. 14 is a simplified diagram of an embodiment of an epicardial lead implanted in a pericardial space.

Referring now to FIGS. 13-15, the interaction of a passive fixation member with the pericardial and epicardial layers in the pericardial space will be discussed in more detail. FIG. 13 illustrates a side view, for example with respect to the view of FIG. 1, of an embodiment of an epicardial lead 1300 and associated passive fixation member 1302. FIG. 13 illustrates as discussed above that the fixation member 1302 may have a relatively flat profile in at least one dimension.

FIG. 14 illustrates an example of how the epicardial lead 1300 may be implanted within the pericardial space S of a heart H. FIG. 14 provides a simplified cutaway view of the heart H illustrating portions of the myocardium M, the epicardial layer EL and an outer pericardial layer PL.

The distal portion of the epicardial lead 1300 is inserted into the pericardial space S via a hole (e.g., hole 1204 in FIG. 12) in the outer pericardial layer PL. Here, the epicardial lead 1300 was inserted or manipulated whereby the fixation member 1302 expands outwardly within the pericardial space S such that predisposed shape of the fixation member 1302 lies at an orientation that is substantially perpendicular to the view of FIG. 14. That is, the side view of FIG. 13 corresponds to the view of FIG. 14. In addition, a thrombotic mesh material 1406 attached to the epicardial lead 1300 is positioned against the epicardial layer EL.

As depicted in FIG. 14, the outer surface of the heart H tends to be relatively curved. Consequently, when the fixation member 1302 is constructed with sufficient resiliency and flexibility in the appropriate dimensions, the fixation member 1302 may bend as shown in FIG. 14 once it expands in the pericardial space. Here, the pericardial layer PL may push down on outer extremities of the fixation member 1302. In addition, the epicardial layer EL may push up on inner extremities of the fixation member 1302. In response to the mechanical deformation caused by such forces, the resiliency of the fixation member 1302 may cause complementary forces to be imparted on the pericardial layer PL and the epicardial layer EL as represented by lines 1402. This in turn increases the friction between the fixation member 1302 and the two layers. Such frictional force tends to prevent the fixation member 1302 from moving in a lateral direction (e.g., as represented by line 1404) within the pericardial space S. It should be appreciated that this frictional force will tend to prevent a fixation member 1302 from moving in other lateral directions (e.g., into and out of the page of FIG. 14). It also should be appreciated that additional frictional force may be imparted due to a curvature of the pericardial space S in other dimensions (e.g., the dimension into and out of the page of FIG. 14).

Figure 15A:
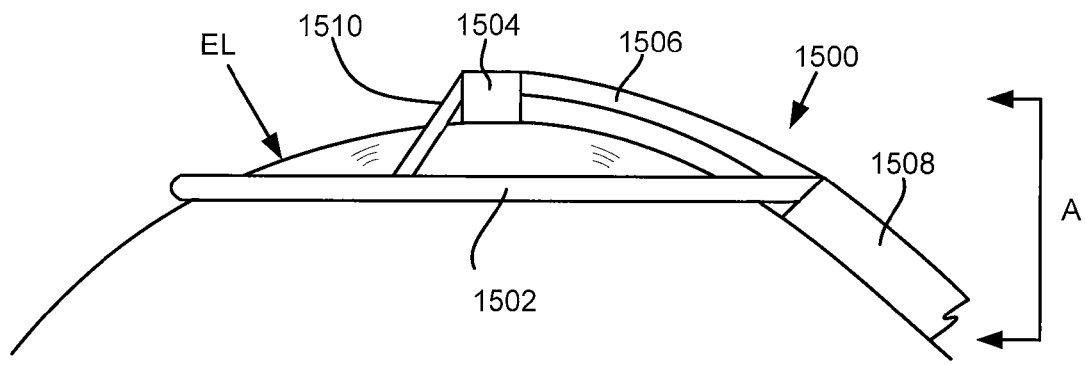
FIGS. 15A and 15B, is a simplified diagram of an embodiment of an epicardial lead implanted on an epicardial layer.

FIG. 15 illustrates an example of how one embodiment of an epicardial lead 1500 with a passive fixation member 1502 may effectively position an electrode 1504 against the epicardial layer EL. FIG. 15A illustrates a simplified side view of one embodiment of the epicardial lead 1500 implanted on a curved epicardial layer EL. The electrode 1504 is mounted on an end of a conductor 1506 that extends from a distal portion of a lead body 1508 of the epicardial lead 1500. The passive fixation member 1502 also extends from the distal portion of the lead body 1508.

Figure 15B:
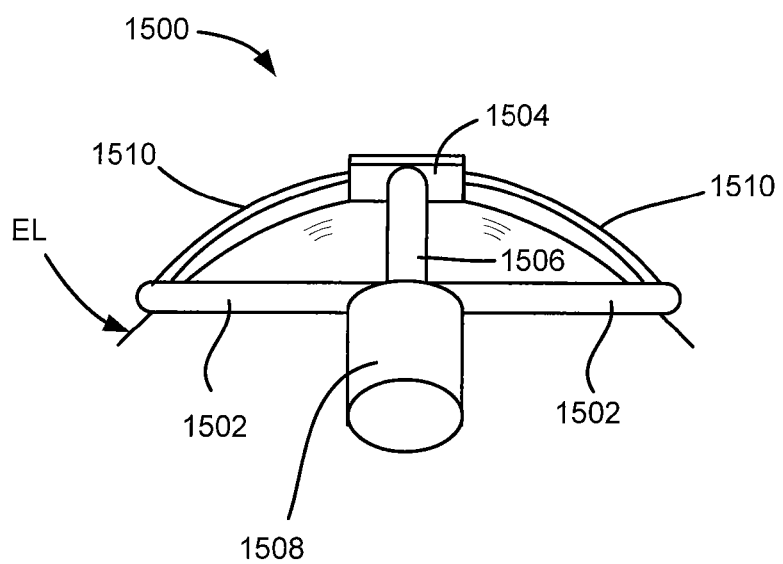

FIG. 15B illustrates the epicardial lead 1500 from the rear view A of FIG. 15A. Here it may be seen that the epicardial layer EL curves in more than one dimension. Moreover, these figures show how the interactions of the passive fixation member 1502 and a pair of structural support members 1510 serve to orient the electrode 1504 in the middle of the shape defined by the fixation member 1502 and serve to firmly hold the electrode against the epicardial layer EL. For example, in the orientation shown in FIG. 15 the structural support members 1510 may be stretched such that they each exert a pulling force on the electrode 1504. This in turn serves to position the electrode in the middle of the fixation member 1502 and serves to pull the electrode down against the epicardial layer EL.

Figure 16:
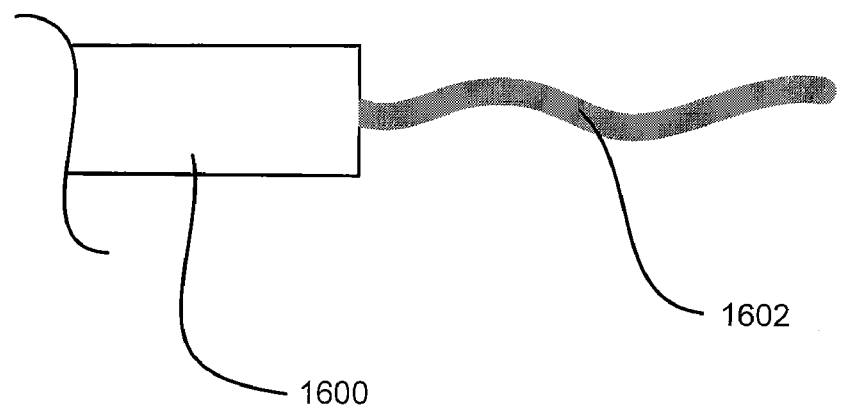
FIG. 16 is a simplified diagram of a view illustrating a substantially flat profile of an embodiment of an implantable epicardial lead.
Figure 17:
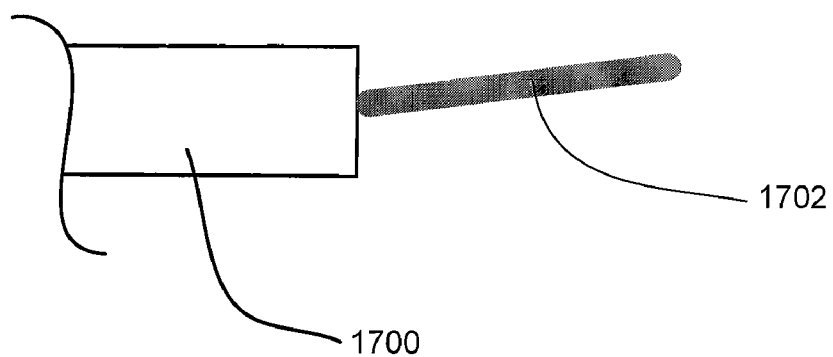
FIG. 17 is a simplified diagram of a view illustrating a substantially parallel profile of an embodiment of an implantable epicardial lead.

It should be appreciated that various relative orientations may be provided between an epicardial lead and an associated passive fixation member (e.g., a mechanical fixture or a shocking coil) depending upon the needs of a particular application. For example, as illustrated in the side view of FIG. 16 in some embodiments an epicardial lead 1600 may incorporate a passive fixation member 1602 that has a substantially, but not entirely, flat profile. Here, a nonlinear profile may, for example, advantageously enable the fixation member 1602 to seat more securely within the pericardial space. As illustrated in the side view of FIG. 17, in some embodiments an epicardial lead 1700 may incorporate a passive fixation member 1702 that extends substantially, but not entirely, parallel to or along the longitudinal axis of the epicardial lead 1700. Such a profile may, for example, enable the epicardial lead 1700 to more effectively be routed through or positioned within the pericardial space.

Figure 18:
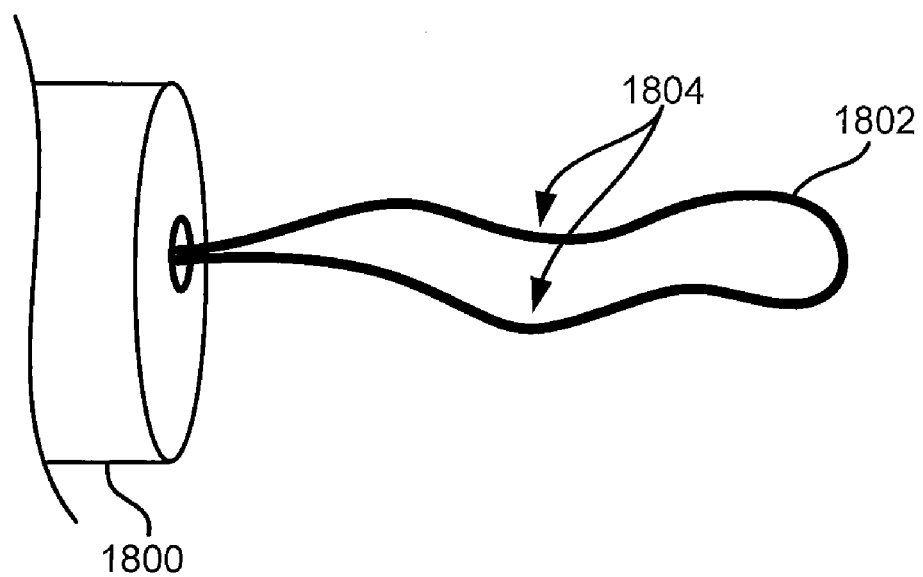
FIG. 18 is a simplified diagram of a view illustrating an embodiment of an implantable epicardial lead with a three-dimensional passive fixation member.

FIG. 18 illustrates an example of lead 1800 incorporating a three-dimensional passive fixation member 1802 (e.g., a mechanical fixture or a shocking coil). In this example, the member 1802 includes several humps 1804 that define a number of pressure points that may serve to anchor the lead within the pericardial space. For example, the humps may serve to force the electrodes on the member or coupled to the member (e.g., in the interior of the loop as discussed herein, not shown) into contact with the epicardial surface of the heart.

Figure 19:
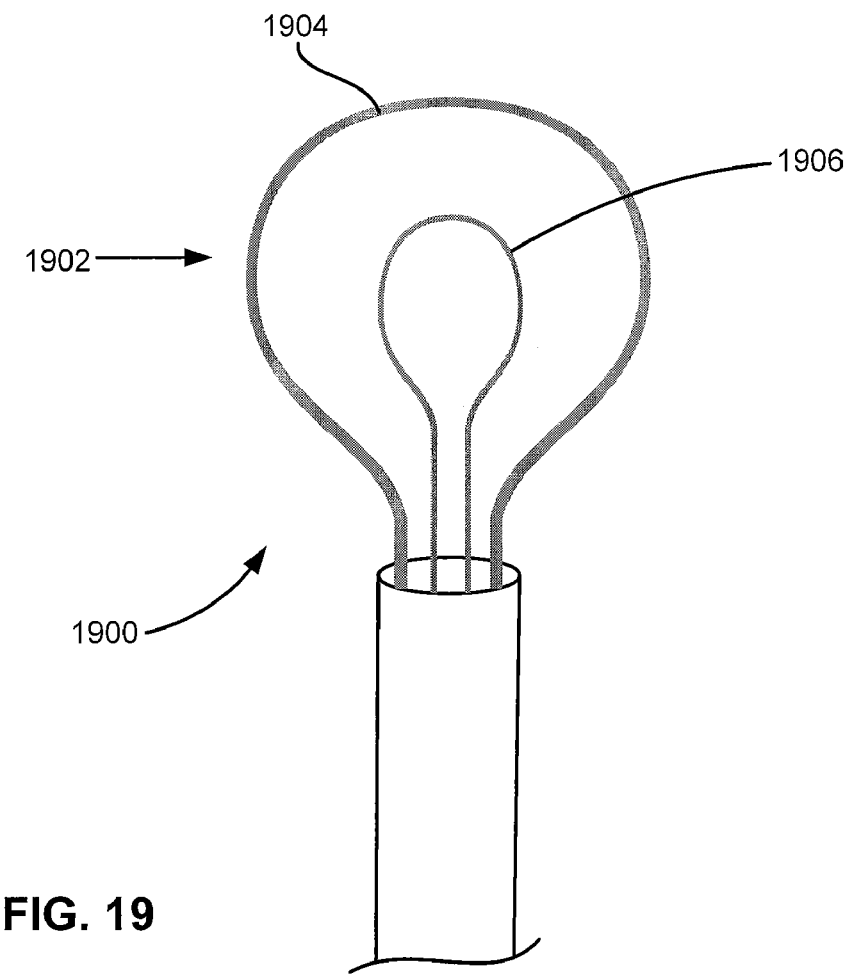
FIG. 19 is a simplified diagram of an embodiment of an implantable epicardial lead including a passive fixation member defining an outer closed shape and an inner closed shape.

In some embodiments a passive fixation member may comprise more than one component. For example, in the embodiment of FIG. 19 an epicardial lead 1900 may comprise a compound passive fixation member 1902 including a first passive fixation member 1904 that it is relatively large. To provide improved mechanical and/or the electrical characteristics, the fixation member 1902 also includes a second passive fixation member 1906.

For example, in an embodiment where the fixation member 1902 comprises a shocking coil, a second coil 1906 may provide additional surface area to carry additional shocking current to the heart. In this way, adverse effects associated with, for example, a "dead zone" in the middle of the first shocking coil 1904 may be alleviated or eliminated. In some embodiments the two coils 1904 and 1906 may be coupled to a common conductor. Alternatively, each coil 1904 and 1906 may be coupled to independent conductors.

Figure 20:
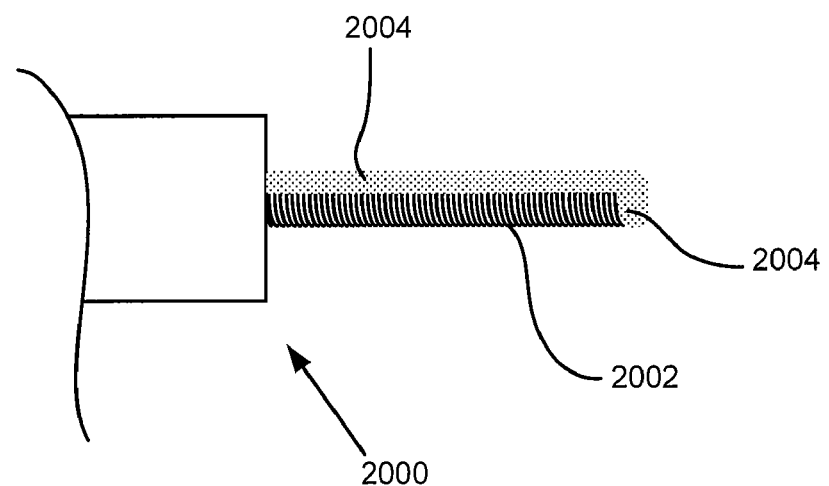
FIG. 20 is a simplified diagram of an embodiment of an implantable epicardial lead including a shocking coil incorporating insulators.

In some embodiments provisions may be made to add directionality to the signals generated by a shocking coil. For example, referring to FIG. 20 in some embodiments an epicardial lead 2000 includes a shocking coil 2002 that is adapted to radiate in specific directions. To this end, an insulator (e.g., an insulation material such as silicone or some other suitable material) 2004 is applied to a portion (e.g., the top) of the shocking coil 2002. In this way, energy losses in undesirable directions (e.g., away from the heart and/or toward sensitive tissue and/or nerves) may be mitigated.

A variety of techniques may be used to incorporate the insulator 2004 into the shocking coil 2002. For example in some embodiments the insulator 2004 may initially be applied to the entire shocking coil 2002. A tool (e.g., a laser) may then be used to cut away portions of insulator 2004 where it is desired to expose the shocking coil 2002. Alternatively, in some embodiments the insulator 2004 may only be applied to a specific portion of the shocking coil 2002.

Figure 21:
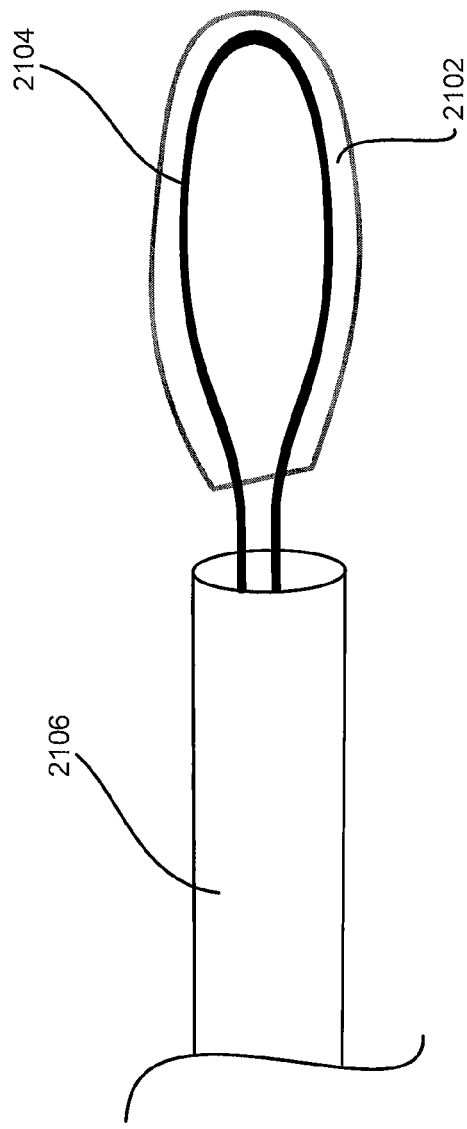
FIG. 21 is a simplified diagram of an embodiment of an implantable epicardial lead including an insulator for a shocking coil.
Figure 22:
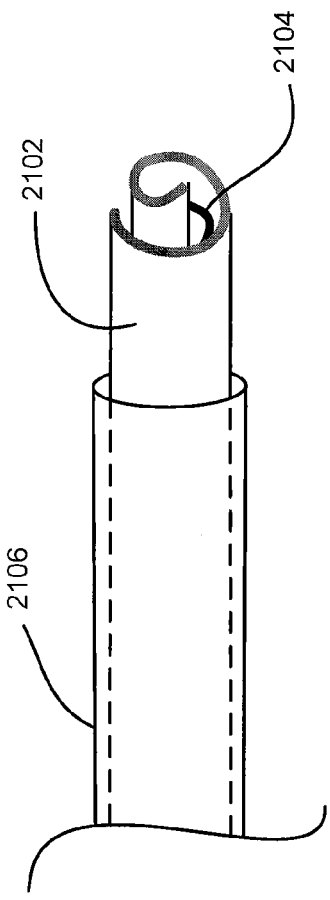
FIG. 22 is a simplified diagram of the implantable epicardial lead of FIG. 21 inserted into a delivery instrument.

Referring now to FIGS. 21 and 22, in some embodiments an insulator sheet 2102 may be applied on one side of a shocking coil 2104. In this case, when the shocking coil 2104 is inserted in the pericardial space the shocking coil 2104 will be manipulated so that the insulator sheet 2102 is on the outer side (e.g., toward the outer pericardial layer) of the shocking coil 2104. During implant, the insulator sheet 2102 may be rolled up or folded up as shown in FIG. 22 to enable the shocking coil 2104 and insulator sheet 2102 assembly to be routed through a delivery instrument 2106.

It should be appreciated from the above that the various structures and functions described herein may be incorporated into a variety of apparatuses and implemented in a variety of ways. For example, a passive fixation member (e.g., a mechanical structure or a shocking coil) as taught herein may be implemented in various sizes and/or using various geometries. A passive fixation member may comprise or include one or more shocking electrodes and/or one or more sensing electrodes. A passive fixation member may thus be constructed of conductive and/or non-conductive materials.

An implantable epicardial lead and associated components as taught herein may take various forms and be constructed of various materials. For example, a lead body and structural support members may be constructed of silicone, polyurethane or any other suitable biocompatible lead material to facilitate chronic implant in the heart. In some embodiments a pacing and/or sensing electrode and/or a shocking coil may be constructed of a platinum-iridium alloy, MP35N or some other suitable material. The materials and manner of construction also may impart sufficient fatigue resistance to facilitate chronic implant in the heart and may impart sufficient flexibility and resiliency to provide desired mechanical characteristics as described herein. Accordingly, it should be appreciated that various types of suitable components may be incorporated into a lead in accordance with the teachings herein.

A lead and associated components may be implemented in a variety of ways. For example, some of the components (e.g., the passive fixation member, the structural support member, the thrombotic material, the electrode, the insulator, etc.) may be coupled using adhesives, mechanical restraint, welding, bonding (e.g., bonded silicone components) or using any other suitable technique. In some embodiments a conductor may be formed of a multi-stranded coil. In some embodiments an electrode may be attached to or incorporated into a conductor. It should thus be appreciated that other types of implementation techniques may be used to provide a lead in accordance with the teachings herein.

The recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

While certain exemplary embodiments have been described above in detail and shown in the accompanying drawings, it is to be understood that such embodiments are merely illustrative of and not restrictive of the broad invention. In particular, it should be recognized that the teachings herein apply to a wide variety of apparatuses and methods. It will thus be recognized that various modifications may be made to the illustrated and other embodiments described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. An implantable epicardial lead, comprising:
    a lead body having a lumen extending there through and an electrical connector at a proximal end;
    an elongated, passive fixation member fixed to a distal portion of the lead body and having a curved portion predisposed to extend from the distal portion of the lead body; the curved portion itself defining a closed or semi-closed loop shape having an interior inside said loop, the curved portion defining the closed or semi-closed loop shape further defining a lumen extending there through in fluid communication with the lumen extending through the lead body, wherein the lumen extending through the curved portion defining the closed or semi-closed loop shape is adapted to accept a stylet;
    a conductor that extends from the distal portion of the lead body and electrically connects with the electrical connector;
    a cardiac sensing and/or pacing electrode coupled to the conductor; and
    at least one structural support member extending from the fixation member to the interior of the closed or semi-closed shape defined by the fixation member to hold the electrode in place within the interior of the closed or semi-closed shape, wherein at least a portion of the at least one structural support member is flexible.

2. The lead of claim 1, wherein the closed or semi-closed loop shape is substantially flat and lies substantially parallel to or along a longitudinal axis of the lead body, wherein the fixation member is flexible and resilient such that the fixation member is adapted to:
   bend to an elongated shape that facilitates insertion of the fixation member into a delivery instrument,
   reorient from the elongated shape to the predisposed closed or semi-closed loop shape, and
   spring back in response to mechanical deformation resulting from force applied in a direction substantially perpendicular to the closed or semi-closed loop shape.

3. The lead of claim 1, wherein the fixation member is predisposed to define a semi-closed loop shape.

4. The lead of claim 3, wherein the fixation member is adapted to bend to a substantially linear shape to facilitate insertion of the fixation member into a delivery instrument.

5. The lead of claim 3, wherein the semi-closed loop shape comprises a substantially closed loop.

6. The lead of claim 1, wherein the fixation member is predisposed to define a loop shape.

7. The lead of claim 1, wherein the fixation member comprises a plurality of predisposed bends to define the closed or semi-closed loop shape.

8. The lead of claim 1, comprising a thrombotic material adapted to promote fibrosis to fix the lead to heart tissue.

9. The lead of claim 1, comprising a material having a rough, porous surface attached to the lead body and/or the conductor, wherein the material is adapted to promote fibrosis to fix the lead to heart tissue.

10. The lead of claim 1, wherein the fixation member is configured to transition along its longitudinal axis between a normally curved shape and an elongated shape.

11. The lead of claim 1, wherein the fixation member comprises a shocking coil.

12. The lead of claim 1, comprising a second electrode coupled to a second conductor that extends from the distal portion of the lead body, wherein the electrode and the second electrode comprise a bipolar electrode.

13. The lead of claim 1, wherein the at least one structural support member is further adapted to maintain the electrode at a desired orientation relative to epicardial tissue upon implant.

14. The lead of claim 1, wherein the at least one structural support member comprises a plurality of structural support members.

15. The lead of claim 1, wherein:
   the fixation member is predisposed to define a loop shape; and
   the at least one structural support member comprises a plurality of structural support members.

16. The lead of claim 15, wherein the fixation member comprises a shocking coil.

17. The lead of claim 1, wherein the passive fixation member has a non-linear profile.

18. The lead of claim 1, wherein the passive fixation member has a substantially flat profile and extends substantially, but not entirely, parallel to or along a longitudinal axis of the lead body.

19. The lead of claim 1, wherein the passive fixation member has a three-dimensional profile including a plurality of humps.

* * * * *